United States Patent [19]

Kubo et al.

[11] Patent Number: 4,898,998

[45] Date of Patent: Feb. 6, 1990

[54] PROCESS FOR PRODUCING BROMINATED ACENAPHTHYLENE CONDENSATES

[75] Inventors: Masashige Kubo; Hideo Sakka; Yukihiro Tsutsumi, all of Yamaguchi, Japan

[73] Assignee: Toyo Soda Manufacturing Co., Ltd., Shinnanyo, Japan

[21] Appl. No.: 615,541

[22] Filed: May 31, 1984

[30] Foreign Application Priority Data

| Jun. 1, 1983 | [JP] | Japan | 58-95830 |
| Oct. 28, 1983 | [JP] | Japan | 58-201119 |
| Oct. 29, 1983 | [JP] | Japan | 58-201920 |
| Nov. 15, 1983 | [JP] | Japan | 58-213326 |
| Dec. 27, 1983 | [JP] | Japan | 58-244796 |
| Feb. 23, 1984 | [JP] | Japan | 59-31451 |

[51] Int. Cl.$^4$ ............................................. C07C 17/00
[52] U.S. Cl. .................. 570/204; 204/157.99; 526/75; 526/280; 526/296; 528/397; 528/495; 528/496; 528/498; 570/193; 570/197; 570/199; 570/200; 570/206; 570/211
[58] Field of Search .................... 204/163 R; 570/193, 570/197, 200, 199, 206, 204, 211; 526/75, 280, 296

[56] References Cited

U.S. PATENT DOCUMENTS

| 2,768,147 | 10/1956 | Meirs et al. | 526/280 |
| 3,448,156 | 6/1969 | Taussig et al. | 570/197 |
| 3,833,674 | 9/1974 | Brackenridge | 570/211 |
| 3,845,146 | 10/1974 | Moore et al. | 570/206 |
| 4,089,843 | 5/1978 | Rausch | 528/498 |
| 4,373,046 | 2/1983 | Hagwara et al. | 526/280 |
| 4,394,484 | 7/1983 | Jenkner et al. | 526/75 |
| 4,423,262 | 12/1983 | Jackisch | 570/193 |

FOREIGN PATENT DOCUMENTS

| 2950877 | 6/1981 | Fed. Rep. of Germany | 570/206 |
| 3010320 | 10/1981 | Fed. Rep. of Germany | 570/200 |
| 106227 | 8/1980 | Japan | 526/280 |
| 3497 | 6/1981 | Japan | 528/498 |
| 358308 | 1/1973 | U.S.S.R. | 570/204 |
| 986634 | 3/1965 | United Kingdom | 570/200 |

OTHER PUBLICATIONS

Y. Morita et al, J. Applied Polymer Science, vol. 27, 3329–3339 (1982).

Primary Examiner—Werren B. Lone
Attorney, Agent, or Firm—Oblon, Spivak, McClelland, Maier & Neustadt

[57] ABSTRACT

A process for producing brominated acenaphthylene condensates of the formula:

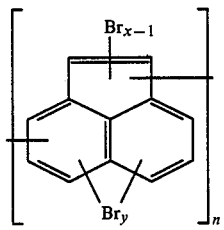

wherein x is 1 or 2, y is an integer from 1 to 6 and n is 1 or more, from elementary units of the following formulas:

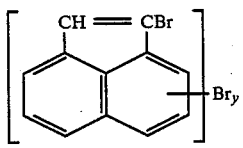

and/or

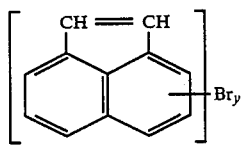

wherein y is as defined above, comprising, (A) brominating the side chain of the acenaphthene with 0.2 to 2.0 times as many moles of bromine as acenaphthene, said (Abstract continued on next page.)

$\delta_H$ (ppm)

bromination initiated by ultraviolet radiation or by a radical initiator in a halogenated hydrocarbon solvent, (B) adding a Lewis acid catalyst to the reaction solution of step (A) to promote the condensation of the brominated acenaphthene product of step (A), (C) adding to the reaction solution of step (B) an equimolar or more amount of bromine relative to the amount of acenaphthene starting material, to further brominate and condense the brominated acenaphthene and/or brominated acenaphthene condensates; and (D) dehydrobrominating the brominated acenaphthene condensates.

13 Claims, 3 Drawing Sheets

PROCESS FOR PRODUCING BROMINATED ACENAPHTHYLENE CONDENSATES

BACKGROUND OF THE INVENTION

1. Field of the Invention

The present invention relates to a novel process for producing brominated acenaphthylene condensates (Con-BACN) starting from acenaphthene, more particularly for producing brominated acenaphthylene condensates having a general formula,

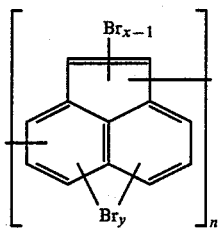

(x represents an integer from 1 to 2, y from 1 to 6 and n 2 or more), more specifically having an elementary unit as defined below:

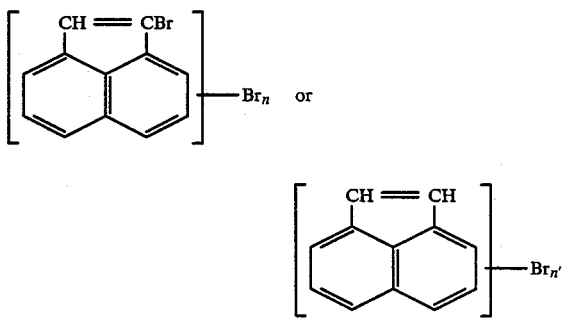

(n and n' are integers between 1 and 6). Further, the present invention relates to a process for separating and recovering brominated acenaphthylene condensates in powder form.

In recent years, it has been a general trend to apply a fire-retarding treatment to inflammable resins such as polyethylene, polypropylene and ethylene-propylene rubber from the standpoint of fire-prevention, and addition of various fire-retarding agents to resins is known for that purpose. Further, wires and cables as well as various instruments used in atomic reactors, breeder reactors and ionization radiation generators are necessarily fire-retarding from the standpoint of safety. Therefore, insulation coating materials and various resin compositions used for these wires must be not only fire-retarding but also radiation-resistant.

Brominated acenaphthylene condensates which are known as excellent compounds having good fire-retarding and radiation-resistant properties could be grafted to a resin by applying free radical generation treatment due to the double bonding in their molecules. In addition, due to the nature of condensates they are highly miscible with resins and can maintain the fire-retarding and the radiation-resisting properties consistently for a long time (Japanese Patent Laid-Open Application No. Sho 56-122862).

The present invention aims to provide a process for producing brominated acenaphthylene condensates which are excellent in their radiation-resisting and fire-retarding properties.

2. Description of Prior Art

A known method to produce brominated acenaphthylene condensates comprises bromination and condensation of acenaphthene to prepare brominated acenaphthene condensates, followed by dehydrobromination.

Previously proposed methods of preparing brominated acenaphthene condensates are as follows: acenaphthene is brominated and condensed at the same time using iron (III) chloride as catalyst and 6 times as much moles of bromine as the acenaphthene at a reaction temperature between 25° and 30° C. (Y. Morita and M. Hagiwara, J. Appl. Polym. Sci., 27, 3329(1982); and brominated acenaphthene containing bromines at the aryl- and benzyl-positions of acenaphthene are condensed in the presence of a catalyst (Japanese Patent Laid-Open Application No. Sho 56-122862). The brominated acenaphthene condensates thus produced are treated with potassium hydroxide-methanol and others to obtain brominated acenaphthylene condensates.

In the former method, however, where the bromination reaction proceeds parallel to the condensation reaction, a large amount of polybrominated by-products of acenaphthene monomers is produced, leading to a low yield of the brominated acenaphthylene condensates.

In the latter method, proposed are the methods involving condensation of, for example, 1,2,3,5-tetrabromoacenaphthene using tin (IV) chloride or sulfuric acid as catalyst. However, the Japanese Patent Laid-Open Application does not refer to the yield and does not teach how to prepare the starting materials.

The present inventors have found on carrying out the above reaction that, due to low reactivity of the species, a significant amount of unreacted monomers remain in the reaction solution, leading to a low yield.

When the reaction was carried out in the presence of an active Lewis acid catalyst such as aluminum chloride, the product composition showed an extremely high degree of condensation, but an unignorable amount of bromine at the benzyl position was lost which was unfavorable to the double bond formation in the dehydrobromination reaction.

Further, the acenaphthene derivative as starting material containing bromines at the aryl- and benzyl-positions can be obtained only by troublesome and difficult processes with a low yield, if industrially readily available acenaphthene is used as raw material of the process.

Production of the brominated acenaphthylene condensates from acenaphthene as raw material, when conducted in a known process, has given only unsatisfactory results as an industrial process owing to the low yield.

The present inventors formerly found, for producing brominated acenaphthylene condensates, to carry out the bromination and condensation of acenaphthene at the same time at a temperature above 60° C. and proposed the process. The preliminary object could be largely attained by the process, but by-production of polybrominated acenaphthene monomers could not be avoided. Therefore, the process did not meet the final object, though a better yield in the productin of the condensates was obtained than that in the previous known process.

The brominated acenaphthylene condensates of this invention are those compounds which contain at least one bromine atom per aromatic ring. Formally, the brominated acenaphthylene condensates are obtained by the condensation reaction of brominated acenaphthene in the course of Friedel-Crafts reaction to give a polymer having a degree of condensation of 2 or more, followed by the dehydrobromination reaction.

In forming the condensates, intermolecular combination is made between carbon atoms at the benzyl-position and those at the aryl-position of acenaphthylene. The benzyl-position in this invention refers to the side chain of the acenaphthene ring and the aryl-position refers to the naphthalene rings.

Examples of the combination are shown in the following formulae:

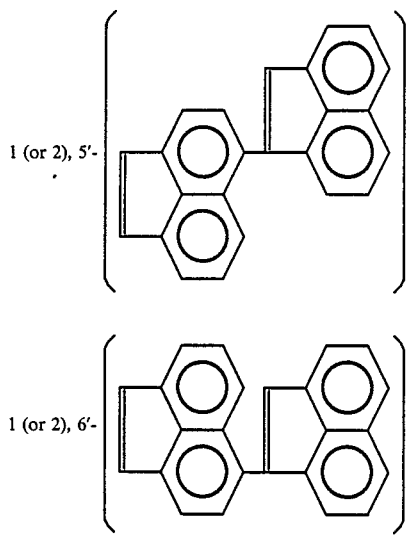

Possible combinations include 1 (or 2), 3'-; 1 (or 2), 4'-; 1 (or 2), 7'-; 1 (or 2), 8'- and so on. Those having the degree of condensation of more than 2 are prepared by increasing the number of unit molecules according to any of these combination.

The condensates aimed at in this invention are a mixture of condensates having a degree of condensation not larger than 10 with good miscibility with resins.

Higher condensates having a degree of condensation greater than 10 show poor dispersion power into and poor miscibility with resin compositions, leading to discouraging effects on administration. On the other hand, monomers remaining uncondensed may likely to cause drawbacks in practice such as adherence to a roller when mixed with a resin and kneaded with the roller, or bleading on the resin surface in the form of pollen-like powder.

In conclusion, a preferred degree of condensation lies in the range from 2 to 9 and this achieved by controlling the reaction condition. However, in the conventional processes, the most predominant products consist mainly of monomers and lower condensates of dimers which are largely susceptible to bleading. Up to now, the degree of condensation has not been able to be controlled in the conventional processes of production.

Regarding dehydrobromination of the brominated acenaphthene condensates, it is known to dropwise add an ethanolic-solution of potassium hydroxide in an aromatic hydrocarbon solvent such as benzene (Japanese Laid-Open Patent Application No. Sho 56-122862) and it is proposed to dropwise add a methanolic solution of potassium hydroxide in a halogenated hydrocarbon solvent such as carbon tetrachloride as proposed by the present inventors in Japanese Patent Application No. Sho 57-169835 (U.S. patent application Ser. No. 537581).

In these methods, when the dehydrobromination is carried out with potassium hydroxide dissolved in a lower alcohol, a nucleophilic substitution reaction of the alkoxyl group occurs competitively and some etheric compounds are formed as by-products. If these by-products contaminate the Con-BACN, the thermal stability of the latter will be lowered so that purification is necessitated in such cases as in the method proposed by the present inventors (Japanese Patent Application No. Sho 57-193145; U.S. patent application Ser. No. 537581).

If potassium hydroxide is replaced by cheaper sodium hydroxide, a larger amount of alcohol is needed because of the smaller solubility of the latter hydroxide and hence a lower concentration of the base inevitably makes the reaction rate slower.

Further, if the dehydrobromination reaction is carried out in an aromatic hydrocarbon solvent, a troublesome operation should be included. Since the preceding reactions, that is bromination and condensation, must be conducted in a halogenated hydrocarbon solvent as an established art, an additional process is required to convert the solvent from a halogenated hydrocarbon to an aromatic hydrocarbon.

Therefore, a process using the same solvent through bromination, condensation and dehydrobromination is more advantageous and profitable.

However, it was found that, when the dehydrobromination is carried out in a halogenated hydrocarbon solvent, a small fraction of the solvent undergoes decomposition. Thus, carbon tetrachloride is decomposed as follows;

$$CCl_4 + 6KOH \rightarrow K_2CO_3 + 3H_2O + 4KCl$$

In addition, an alcoholic solution of potassium hydroxide which is added to a solution of brominated acenaphthene condensates should be prepared by dissolving solid potassium hydroxide in alcohol. This is a cumbersome operation and projects a problem on the worker's safety particularly because the process of this invention involves a batch-type reaction.

Furthermore, the reaction proper proceeds in two phases, that is, a solution of brominated acenaphthene condensates and an alcoholic solution, and therefore as the reaction progresses a large amount of potassium bromide salt is deposited, which adheres on the wall of reaction vessel or blades of stirrer and causes troublesome operations after the reaction.

Thus, as has been described above, the known processes of dehydrobromination are by no means satisfactory from the point of view of quality of products and of economical and operational estimation as an industrial technology.

Further, regarding the process for separating and recovering Con-BACN from the Con-BACN solution produced from acenaphthene as starting material the following methods may be considered;

(1) to distil the Con-BACN solution to remove the solvent; or (2) to add the Con-BACN solution to a poor solvent to precipitate and separate Con-BACN.

However, the method (1) causes resin-like coagulation of Con-BACN so that powder Con-BACN cannot be obtained, and the handling operation is difficult.

Although the resin-like Con-BACN as it stands can be practically used, it contains a small amount of the solvent remaining therein, which is relatively difficult to remove. Therefore, the melting point f the resultant Con-BACN is 50° to 80° C. which is 50° to 70° C. lower than that of the powder Con-BACN, and when admixed with resin by rolls it easily sticks to the rolls and causes corrosion of working and forming machines due to thermal decomposition of the solvent.

In this connection, if the solvent contained in Con-BACN can be removed to obtain powder Con-BACN having a higher melting point, great advantages can be achieved with respect to the handling and roll mixing operation.

Meanwhile, regarding the method (2), it is known to add a solution of Con-BACN to acetone which is one of the poor solvent, and to reprecipitate powder Con-BACN (Y. Morita and M. Hagiwara, J. Appl. Polym. Sci., 27 3329(1982)). However, as Con-BACN will be dissolved in acetone to some degree the Con-BACN obtained by the reaction must preliminarily be condensed and then added to cold acetone (0°--10° C.) for reprecipitation. Therefore, the whole process is complicated and the yield of Con-BACN is low.

Extensive investigations have been conducted on producing brominated acenaphthylene condensates by the present inventors using acenaphthene as raw material, and it has been found with success that side-chain brominated acenaphthenes can be obtained with a high selectivity when acenaphthene is brominated with bromine under the ultraviolet irradition or in the presence of a radical initiator. The products thus obtained are a mixture of mono-, di- and tri-bromides depending on the amount of bromine added, and it has been found that, among the bromides, the monobromide in particular can be readily condensed under a mild condition with catalysts which are called strongly active or even with moderately or less active Lewis acid catalysts and the degree of condensation does not exceed 10, the strongly active Lewis acid catalysts including, for example, $AlCl_3$, $AlBr_3$ and $GaCl_3$ and the moderately or less active ones including $TiCl_4$, $FeCl_3$, $SbCl_5$, $SnCl_4$ and $ZnCl_2$. More particularly, side-chain monobromides could be formed with relatively high selectivity by controlling the amount of bromine to 0.2 to 2.0 times as much in moles as that of acenaphthene. The monobromides thus obtained are subjected to the condensation reaction using a Lewis acid catalyst and the product condensates are brominated using more than an equimolar amount of bromine to the acenaphthene. Thus, bromination reaction of acenaphthene occurs with a good balance between at the aryl- and the benzyl-positions, in parallel with the proceeding condensation reaction. As a result, the inventors found that intermediates of brominated acenaphthylene condensates could be obtained with a high yield of which condensates of the degree of condensation of 2 to 10 were the main constituents, and they could reach the development of this invention.

Further, the present inventors intensively investigated the dehydrobromination reaction and it has been found that when brominated acenaphthene condensates dissolved in a halogenated hydrocarbon solvent is dehydrobrominated with an alkali metal hydroxide, use of a mixture of water and alcohol in which ratio of water to alcohol is 0.1 to 0.5 by weight as the solvent of said alkali metal hydroxide could remarkably overcome the difficulty of previous arts. The present invention has thus come to completion.

In short, the increased concentration of the alkali metal hydroxide according to this invention has made it possible to conduct the dehydrobromination reaction without leading to decreased rate of the reaction due to water addition. In addition, the formerly mentioned side reaction could be remarkably suppressed by using said anhydrous alcohol. Obtained Con-BACN has good quality because the nucleophilic reaction of alkoxyl group disappears. In addition, this process is economically advantageous because decomposition of the halogenated hydrocarbon solvents is markedly suppressed.

In the method of this invention, the operation to dissolve solid caustic alkali is no more needed because the alkali metal hydroxide in an aqueous solution is only added to alcohol to prepare an alkali solution of a desired concentration. This implys remarkable improvement in workability.

Furthermore, when an aqueous alcohol solution is used, the alkali metal salt that is produced in the reaction remains dissolved in the solution and therefore it makes easy the treatment after completion of the reaction.

Thus, the present invention provides a process, as a part of a whole process, for economically producing Con-BACN from brominated acenaphthene condensates by a simple procedure.

Further, the present inventors investigated in details on the dehydrobromination reaction of brominated acenaphthene condensates without using a lower alcohol. It has been found that the dehydrobromination reaction proceeded very slowly without reaching completion if the condensates were dissolved in an organic solvent wich was immiscible with water and brought into contact with an aqueous solution of an inorganic metal baase to react in a two-phase system. They also found that, if the reaction was conducted in a severe condition to accelerate the reaction rate, alcohol derivatives of brominated acenaphthene were produced as by-product which led to lower to yield of Con-BACN. The contaminating alcoholic compounds may probably cause degraded qualities such as thermal stability, and therefore should be prevented.

In the more intensified investigation of the dehydrobromination reaction in the two-phase system, the inventors could reach the conclusion that the reaction could be completed in a shorter period of time when a quaternary ammonium salt was applied as a phase transfer catalyst, while crown ethers when used as the phase transfer catslysts could reveal no effect. Thus they could succeded in remarkable improvement of the known techniques and complete the present invention.

The dehydrobromination reaction in the two-phase system using crown ethers and quaternary ammonium salts as phase transfer catalyst are generally known. However, the known processes may cause various side reactions in the dehalogenation reactions of secondary alkylhalides such as appears in the present invention, and therefore they do not deserve accomplished methods.

For example, A. W. Herriott and others (Tetrahedron Letters, 44, 4521(1972)) found that a reaction of 2-bromooctane with an aqueous solution of sodium hydroxide in the presence of a quaternary ammonium salt in a two-phase system mainly produced octenes by the E2-type elimination reaction but a Sn 2-type substitution reaction occurred as a side reaction to produce 2-octanol in addition to said olefins. C. L. Liotta et al. (J. Am. Chem. Soc., 96, 2250(1974)) found that a non-aqueous reaction of 2-chloro-2-methylcyclohexanone with KF in acetonitrile in the presence of 18-crown-6 caused elimination (69%) and substitution (31%) of the F ion.

Thus, an elimination reaction and a nucleophilic reaction occur competitively in the reaction of a secondary or tertiary alkylhalide with an inorganic metal base in the presence of a phase transfer catalyst so that one cannot predict a single product.

However, in the process of this invention, only the dehydrobromination reaction of brominated acenaphthene condensates occurs selectively, and any by-product formation as a result of nucleophilic reaction is seen and decomposition of halogenated hydrocarbons does not occur, which could not have predicted from previously known arts and provides an industrially very useful process. In other words, the side reactions mentioned above could be completely suppressed by the process of the present invention. More particularly, the present invention does not use any alcohol solvent so that a nucleophilic reaction due to alkoxy group and a by-product of alcohol derivative are not seen at all. Therefore the Con-BACN obtained is of a high quality. In addition, no decomposition of halogenated hydrocarbon means an economical profit.

Again, the process of this invention permits the dehydrobromination reaction of brominated acenaphthene condensates to be completed in a very short period of time under mild conditions. In addition, since the process of this invention is carried out in two phases, organic and aqueous, inorganic metal salts that are formed as the reaction proceeds are dissolved in the aqueous phase and suppressed from depositing so that the treatment after the reaction becomes easier.

Therefore, the process of the present invention is provided as one of the integrated processes for the production of Con-BACN, comprising making brominated acenaphthene condensates dissolved in an organic solvent in contact with an aqueous solution of an inorganic metal base in the presence of a phase transfer catalyst.

Further, the present inventors have conducted extensive studies on various types and kinds of poor solvents for improving the yield of Con-BACN by simple operation in a reprecipitation process for recovering powder Con-BACN using poor solvents, and hae found that it is possible to recover powder Con-BACN by a simple operation yet with a high degree of yield when a monohydric alcohol of saturated aliphatic compounds having 3 to 5 carbon atoms is used.

Therefore, one aspect of the present invention is to provide a process for separating and recovering Con-BACN applicable to the production of Con-BACN solution obtained from acenaphthene through bromination, condensation and dehydrobromination of acenaphthene, which is characterized by adding the Con-BACN solution to a monohydric alcohol of saturated aliphatic compounds having 3 to 5 carbon atoms to precipitate powder Con-BACN.

The present inventors have made further investigations on poor solvents which permit precipitation of powder Con-BACN from the Con-BACN solution at a high degree of yield and also facilitate the separation between the solvents of the Con-BACN solution and the poor solvents, and have found that when the Con-BACN solution is added to a saturated aliphatic hydrocarbon having 5 to 9 carbon atoms powder Con-BACN can be recovered at a relatively high degree of yield and that the saturated aliphatic hydrocarbon can be separated easily by distillation after reprecipitation, because it has a boiling point different from that of the halogenated hydrocarbons or aromatic hydrocarbons used as the solvent of the Con-BACN solution and they don't form azeotropic mixture in distillation.

The present inventors have made still further investigations on the separation and recovery of Con-BACN on a commercial base, and found that powder Con-BACN of high quality can be obtained at a high degree of yield when the following process is repeated. Con-BACN solution using a good solvent is added to a poor solvent of saturated aliphatic hydrocarbons having 5 to 9 carbon atoms and having a boiling point higher than that of the good solvent to reprecipitate powder Con-BACN, then the slurry is removed of the good solvent by distillation, the resultant Con-BACN slurry is filtered to separate the powder Con-BACN and the filtrate is circulated to the poor solvent inthe reprecipitation step.

SUMMARY OF THE INVENTION

The present invention provides a process for producing brominated acenaphthylene condensates, comprising:

(A) a stage of operation in which the side chain of acenaphthene is brominated with 0.2 to 2.0 times as much moles of bromine as the acenaphthene under ultraviolet irradiation or in the presence of a radical initiator in a halogenated hydrocarbon solvent;

(B) a stage of operation where a Lewis acid catalyst is added to the reaction solution in which the bromination was carried out, to condense the brominated acenaphthene;

(C) a stage of operation in which an equimolar or more amount of bromine to the acenaphthene is added to the reaction solution to further brominate and at the same time condense the brominated acenaphthene and brominated acenaphthene condensates; and (D) a stage of operating a dehydrobromination reaction.

The process of the present invention can be summarized by use of following reaction equations:

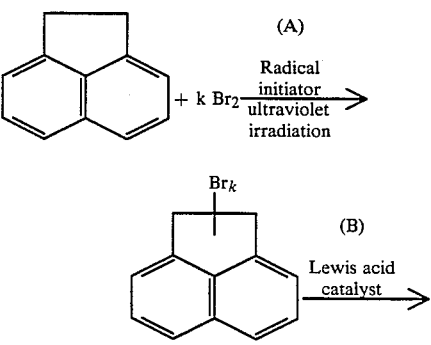

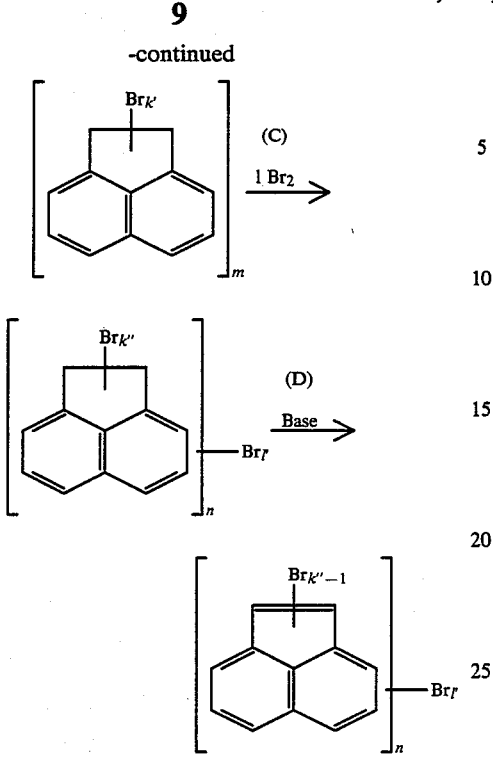

(In the equations, k and k' range from 0.2 to 2.0, k" from 1 to 2, 1 and 1' from 1 to 6 and m and n are each 2 or more.)

The two different reactions, bromination reaction and condensation reaction of acenaphthene, which have been carried out in a single stage in previous processes are separately conducted in the process of this invention. Therefore, by-product of polybrominated monomers does not appear and brominated acenaphthylene condensates could be obtained with a sufficiently high yield. As for the condensation reaction, the reaction occurs under a mild condition using a Lewis acid catalyst with the degree of condensation not exceeding 10, so that the degree of condensation could be more easily controlled than in conventional processes. The obtained brominated acenaphthylene condensates are composed mainly of those of the degree of condensation of 2 or more, therefore characteristic features are the high workability on kneading with resins and no generation of bloom on their shaped surface.

In the bromination reaction of brominated acenaphthene condensates in the second stage, good balance could be maintained between aryl- and benzyl-positions with respect to the bromination, so that the brominated acenaphthylene condensates produced contain a larger percentage of the C=C double bonding at the benzyl-position. Therefore, a high rate can be expected in the graft reaction to resins.

The second object of the present invention is to provide novel processes for dehydrobromination in the production of brominated acenaphthylene prepared from acenaphthene as starting material, one of which processes is characterized in that brominated acenaphthene condensates dissolved in a halogenated hydrocarbon solvent is dehydrobrominated with an alkalimetal hydroxide dissolved in an alcohol containing 0.1 to 0.5 weight part of water, and the other is characterized in that brominated acenaphthene condensates are brought into contact with an aqueous solution of inorganic metal base under the presence of a phase transfer catalyst.

The third aspect of the present invention is to provide a process for separating and recovering powder Con-BACN from Con-BACN solution, which process is characterized in that the solution of brominated acenaphthylene condensates obtained by bromination of acenaphthene followed by condensation and dehydrobromination is added to a monohydric alcohol of saturated aliphatic compounds having 3 to 5 carbon atoms or is added to a saturated aliphatic hydrocarbon having 5 to 9 carbon atoms.

Further, the present invention provides a modified process for separating and recovering powder Con-BACN, which comprises:

Step (A) of adding a solution of Con-BACN dissolved in a good solvent to a solvent having a boiling point higher than that of the good solvent to reprecipitate Con-BACN;

Step (B) of distillate the slurry of Con-BACN obtained in the Step (A) to remove the good solvent; and Step (C) of filtering the slurry distillated in the Step (B) to separate and recover Con-BACN and circulating the filtrate as the poor solvent in the Step (A).

DETAILED DESCRIPTION OF THE INVENTION

The process for the first object of this invention will be described in details.

First in Step (A), acenaphthene is dissolved in a halogenated hydrocarbon solvent and 0.2 to 2.0 times as much moles of bromine as acenaphthene is added under ultraviolet irradiation or in the presence of an initiator to brominate the acenaphthene at the side chain.

The halogenated hydrocarbons to be used in this invention are those solvents which are inert to the reaction, including carbon tetrachloride, chloroform, methylenechloride, ethylenedichloride, ethylenedibromide and trichloroethane. The amount to be used for a run is not particularly restricted, but an amount of the solvent with which enough to dissolve the total amount of the raw material acenaphthene is usually applied to assure a homogeneous reaction.

For the reaction, ultraviolet irradiation or a radical initiator is employed. The two may be combinedly applied. The radical initiator is selected from those which form a radical on thermal decomposition. Peroxides and azo compounds to be used at temperatures ranging from 30° to 150° C. are preferably selected. They include, for example, benzoyl peroxide, acetyl peroxide, lauroyl peroxide, and azo-bis (isobutyro)nitrile. Radical initiators are applied in an amount of 0.1 to 50 molar %, preferably 1 to 20 molar %, against acenaphthene.

Usually a mercury lamp is used as light source of ultraviolet ray, including the low-, high- and uper high-pressure mercury lamps. The ultraviolet ray is irradiated to the acenaphthene solution (a) by the external irradiation method in which a ultraviolet light source is placed outside of the vessel of solution, or (b) by the internal irradiation method in which a mercury lamp is immersed in the acenaphthene solution. Either may be applicable.

In the presence of a radical initiator or under ultraviolet irradiation, bromine is added to acenaphthene for bromination.

The bromine is introduced in the side chain of acenaphthene with a high selectivity when the reaction temperature exceeds 30° C., preferably 60° to 150° C.

Successive reactions occur at the side chain, producing monobromide, dibromide, and then tribromide successively. Selectivity of the monobromide in these successive reactions could be enhanced by controlling the percentages of bromination of acenaphthene. Thus, the amount of bromine added should be selected to 0.2 to 2.0 times, preferably 0.5 to 1.5 times, as much as acenaphthene in moles. When the amount of bromine added is less than 0.2 times, only poor formation of bromide results, which necessarily leads to lowered effect in the following condensation reaction. On the other hand, if the amount of bromine exceeds 2.0 times, di- and tri-bromides will occupy the main proportion of the reaction products and also lower the effect of the following condensation reaction.

In the condensation reaction in Step (B) that follows, the side-chain brominated acenaphthenes are condensed by adding a Lewis acid catalyst without isolating said side-chain brominated acenaphthenes. The catalyst Lewis acids are usually selected from metal halogenides. They include, for example, $AlCl_3$, $AlBr_3$, $AlI_3$, $GaCl_3$, $GaBr_3$, $InCl_3$, $InBr_3$, $SnCl_4$, $FeCl_3$, $TiCl_4$, $ZrCl_4$, $RuCl_3$, $SbCl_5$, $SbF_5$, $WCl_6$, $ZnCl_2$, $BCl_3$ and $BF_3$. To suppress various side reactions that may accompany, relatively less active catalysts such as $TiCl_4$, $FeCl_3$, $SnCl_4$, $SbCl_5$ and $ZnCl_2$ are particularly preferred. The amount of addition of these catalysts may be arbitrarily selected in the range from 0.01 to 0.5 mole per a unit mole of acenaphthene as reaction substrate, but a range from 0.05 to 0.2 mole is preferable from the point of the reaction efficiency. For an amount less than 0.01 mole, the condensation reaction proceeds very slowly and the reaction remains incompleted. On the other hand, an amount larger than 0.5 mole is not effective to accelerate the reaction velocity and therefore does not pay economically. The condensation reaction is usually carried out at a temperature ranging from 0° to 100° C., preferably from 10° to 80° C. The reaction takes usually from 10 min. to 8 hours, depending on reaction temperature and other factors.

In the reaction solution resulting from the condensation reaction which has been carried out with the side-chain brominated acenaphthene in the presence of a Lewis acid catalyst, contained are condensates of acenaphthene having the degree of condensation ranging from 2 to 8, as well as monomers of brominated acenaphthene. The monomers of brominated acenaphthene should be condensed, and this is carried out simultaneously in the following bromination stage.

To the solution resulting from Step (B) in which brominated acenaphthene has been condensed, bromine is added in Step (C) in an amount more than equimolar to the starting acenaphthene, to further brominate, as well as to further condense, the brominated acenaphthene condensates. Advantageously, this bromination reacton is carried out immediately after the condensation reaction in the presence of the same Lewis acid catalyst. Exceptionally if the catalyst used for the condensation works only weakly for the bromination, a more active catalyst may be added to promote the bromination reaction.

The amount of addition of bromine should be more than equimolar, preferably more than twice as much, against acenaphthene. If the amount is smaller than equimolar, bromination occurs preferentially at the aryl position and therefore the brominated acenaphthylene condensates which are aimed at could not be obtained. Furthermore, compounds obtained exhibit only insufficient effect as fire-retarding agent due to the low bromine content. On the other hand, if the amount of bromine exceeds 5 times as much in moles, recovery of the excessive bromine will make economical disadvantages. The maximal preferred amount of bromine should be 5 times as much in moles.

Temperatures between 10° and 80° C. are preferred as the reaction temperature of bromination. In this range of temperature, a good balance can be maintained between aryl- and benzyl-positions in the bromination reaction, and the condensation reaction occurs concurrently, so that this process gives with a high yield the product of condensates which are brominated either at the benzyl position or at the aryl position and having the degree of condensation of 2 to 10.

At last in Step (D), the brominated acenaphthene condensates thus produced are dissolved in an inert solvent, to which a base such as potassium-methanol is added to cause the dehydrobromination reaction for producing the brominated acenaphthylene condensates.

As has been described above, the present invention starts using readily available raw materials and makes it possible to produce brominated acenaphthylene condensates in a simple process with a high yield, while the process proceeds in a single reaction vessel without isolating intermediate products in each step. Thus this invention permits an economically profitable process for producing brominated acenaphthylene condensates.

The brominated acenaphthylene condensates obtained by the process of this invention mostly consist of those condensates having the degree of condensation of 2 to 8 as major constituents. They are excellent in the roll-workability in kneading with resins and in the miscibility with resins, and they do not generate blooms. In addition, they contain quantitatively formed $C\!=\!C$ double bonds at the benzyl position and are excellent in the efficiency of grafting to resins, radiation resistance and the fire-retarding property.

The new process for dehydrobromination using water-containing alcohol according to the second effect of the present invention will be described hereinbelow.

The halogenated hydrocarbons to be used in this process are solvents which are inert to reactions of bromination, condensation and dehydrobromination of acenaphthene. They include, for example, carbon tetrachloride, chloroform, methylenechloride, ethylenedichloride, ethylenedibromide and trichloroethane. Among them carbon tetrachloride is preferable.

No restriction is laid to the amount of a solvent used, but a total amount of brominated acenaphthene condensates is preferably dissolved in the solvent, so that that amount of a solvent is used in which Con-BACN produced amounts to 10 to 70% by weight of the solvent.

The alkali metal hydroxides to be used in this invention may include hydroxides of lithium, sodium, potassium and caesium, but usually sodium and potassium hydroxides are selected from the economical standpoint. The amount of the alkali metal hydroxide used should be not less than 0.8 mole, preferably 1 to 3 moles, per mole of the structural unit of the brominated acenaphthene condensates.

In this invention hydrous alcohols are used as solvent for alkali metal hydroxides, so that the alcohols employed are those which contain 4 or less carbon atoms and are more miscible with water. They include, for example, methanol, ethanol, n-propanol, isopropanol, n-butanol, sec-butanol, tert-butanol, ethyleneglyciol and propyleneglycol. Among them, methanol and ethanol are preferable because of the rapid reaction and easy treatment after the reaction.

The applied amount of these lower alcohols should be more than that required, as a mixture with water, to dissolve the alkali metal hydroxide completely, but a rather small amount is preferred so as to maintain a high concentration of the alkali metal hydroxide used to accelerate the reaction and to make easier the recovery of the alcohol.

The amount of water to be added to an alcohol is selected so that the ratio of water to alcohol is 0.1 to 0.5 by weight. The range from 0.2 to 0.4 is more preferred. For the ratio water to alcohol being less than 0.1 by weight, the dehydrobromination reaction is often accompanied by the forementioned side reactions, that is the nucleophilic reaction by alkoxyl group and the decomposition of a halogenated hydrocarbon solvent. On the other hand, for the ratio being greater than 0.5 the reaction becomes extremely slow and does not reach completion.

At the amount of water added in this invention, the reaction proceeds rapidly enough and is completed with a quantitative yield. Further the above-mentioned side reactions are markedly suppressed.

Reactions are usually conducted under a normal pressure, so that the temperature of reactions is below the boiling point of the solvent and usually selected at 30° to 100° C. Generally speaking, a higher temperature is preferred because reactions proceed faster and more quantitatively.

The reactions usually take 10 min. to 8 hours depending on the temperature at which the reactions take place.

After the completion of reactions, Con-BACN produced can be isolated in powders by a known method. For example, the reaction mixture is washed with water and the organic phase is added to a poor solvent such as acetone, to separate the Con-BACN by reprecipitation. Thus, the Con-BACN can be obtained in powdery form.

In the process proposed by this invention, Con-BACN of high quality could be economically produced from brominated acenaphthene condensates in a simple procedure. Thus the present invention can provide a process much simplified compared with the conventional processes and having industrial advantages for production of Con-BACN.

Hereinbelow, the process of dehydrobromination using an aqueous solution of inorganic metal base under a phase transfer catalyst will be described in detail.

The process of this invention can be explained using following reaction formula:

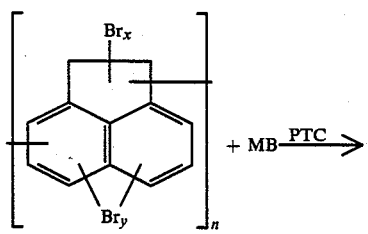

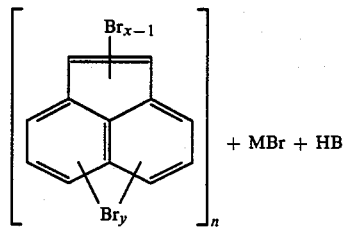

(where MB is an inorganic metal base, PTC is a phase transfer catalyst, x is an integer 1 or 2, y is an integer ranging from 1 to 6 and n is an integer).

Brominated acenaphthene condensates dissolved in an organic solvent are brought into contact with an aqueous solution of an inorganic metal base in the presence of a phase transfer catalyst to dehydrobrominate the condensates.

The inorganic metal bases to be used in this invention are preferably hydroxides, carbonates or hydrogen carbonates of alkali metals or alkali earth metals. But they are generally hydroxides, carbonates and hydrogen carbonates of lithium, sodium, potassium, magnesium, calcium or barium. Most preferable are sodium hydroxide or potassium hydroxide. The amount to be used is selected to be more than equimolar, preferably 1 to 3 times as much in moles, against the structural units of the raw material brominated acenaphthene condensates.

Concentrations of the aqueous solution may be arbitrarily determined between 1 to 50% by weight approximately. However, the reaction rate tends to be lower slightly when a dilute solution is applied. Therefore, a concentration from 5 to 40% by weight is preferred from the practical standpoint.

A quaternary ammonium salt is used as catalyst, or phase transfer catalyst. Quaternary ammonium salts may be any ones which are not cited in this invention. They include, for example, chlorides, bromides, iodides or hydroxides of benzyltrimethylammonium, benzyltriethylammonium, benzyltripropylammonium, phenyltriethylammonium, tetramethylammonium, tetraethylammonium, tetrabutylammonium, triethylpropylammonium, tetrapentylammonium, trioctylmethylammonium, octyltrimethylammonium, lauryltrimethylammonium, hexadecyltrimethylammonium, 2-hydroxyethyltrimethylammonium, 3-phenoxybenzyltriethylammonium. Among them the most excellent in the reaction efficiency are salts of tetrabutylammonium, tetrapenthylammonium, trioctylmethylammonium and octyltrimethylammonium.

The amount of these catalyst to be added may be larger than 0.0001 mole per structural unit of the brominated acenaphthene condensates as reaction substrate, but preferably from 0.001 to 0.1 mole per unit from the point of reaction efficiency.

The organic solvents to be used in this invention refer to those solvents which are immiscible with water and dissolve brominated acenaphthene condensates. The solvents are selected from halogenated hydrocarbons and aromatic hydrocarbons which are inert in the dehydrobromination reaction. They include, for example, carbon tetrachloride, chloroform, methylene chloride, ethylenedichloride, ethylenedibromide, chlorobenzene, benzene, toluene, xylene and ethylbenzene. Concentrations of brominated acenaphthene condensates are not particularly restricted, but usually solutions of about 5 to 70% by weight are used.

Contact of the organic phase with the aqueous phase in a vessel is made by stirring or by shaking.

The temperature of reacton is generally below the boiling point of the solvent used, because the reaction is carried out under the normal pressure, and therefore is selected from the room temperature to 120° C. In general, a higher temperature is preferable since the reaction proceeds faster and more quantitatively. The time of reaction depends on the temperature at which the reaction occurs, but usually it takes about 10 min. to 8 hours.

After the completion of reaction, Con-BACN formed can be isolated by any known method in a powdery form. For example, the reaction mixture is washed with water to separate the aqueous phase and the organic phase is added to a poor solvent such as acetone, to separate the Con-BACN by reprecipitation. Thus, the Con-BACN is obtained in a powdery form.

In this way Con-BACN of a high quality can be prepared by the method of this invention from brominated acenaphthene condensates in a simple procedure and economically.

Hereinbelow detailed description will be made on the process for separating and recovering powder Con-BACN according to the present invention.

The organic solvent for the Con-BACN solution from which the powder Con-BACN is separated and recovered means a good solvent which dissolves Con-BACN and includes halogenated hydrocarbons or aromatic hydrocarbons which are inert in the dehydrobromination reaction. For example, carbontetrachloride, chloroform, methylenechloride, ethylenedichloride, ethylenedibromide, chlorobenzene, benzene, toluene, xylene, ethylbenzene, etc. may be used.

Regarding the concentration of the Con-BACN solution, there is not specific limitation, and normally a concentration from 5 to 70% by weight is used.

The monohydric alcohol of saturated aliphatic compounds having 3 to 5 carbon atoms includes: 1-propanol, 2-propanol, 1-butanol, 2-methyl-1-propanol, 2-methyl-2-propanol, 1-pentanol, 2-pentanol, 3-pentanol, 2-methyl-1-butanol, 3-methyl-1-butanol, 2-methyl-2-butanol, 3-methyl-2-butanol and 2,2-dimethyl-1-propanol, etc.

However, from the feasbility of drying the powder Con-BACN after the reprecipitation and the commercial availability, 1-propanol, 2-propanol, 1-butanol, 2-butanol and 2-methyl-2-propanol are preferable in practice.

Alcohols having two or less carbon atoms provide only poor dispersibility for Con-BACN and cannot precipitate Con-BACN in the solid state. Meanwhile, alcohols having six or more carbon atoms tend to increase the solubility of Con-BACN, thus lowering the yield ratio of Con-BACN. Also, polyhydric alcohols di- or higher hydric alcohols ahve a higher boiling point so that the resultant powder Con-BACN cannot easily be dried.

The amount of the monohydric alcohol of saturated aliphatic compounds to be used is normally 1 to 20 times, preferably 2 to 10 times by volume of the Con-BACN solution.

When the amount of the alcohol is less than the amount of the Con-BACN solution, the recovery ratio of Con-BACN is low, while when the amount of the alcohol is more than 20 times of the amount of the Con-BACN solution economical disadvantage will be caused although there is no problem in the reprecipitation. The reprecipitation of Con-BACN is performed by adding the Con-BACN solution to the alcohol, preferably under stirring. However, in this case ordinary stirring sometimes causes partial solidification of Con-BACN to form crystals which must be crushed. Therefore, shear stirring is more preferable.

The shear stirring herein used includes, for example, forced stirring by screw mixers of two-shaft type and stirring with shearing force as done by a homomixer, and such shear stirring can promote dispersion precipitation due to the forced stirring of the good solvent and the poor solvent for Con-BACN and permits dispersion of the good solvent into the poor solvent so that highly efficient precipitation can be attained.

Thus in the case of a reactor having an ordinary one stirring mechanism, the dispersion is unefficient and the crystal precipitation is slow, but when two mixers are used to promote the dispersion, the contact surface between the good solvent and the poor solvent is increased so that the good solvent remaining in Con-BACN can be extracted in a much shorter time than when they are merely mixed, thus promoting the precipitation, hence achieving a highly efficient precipitation of Con-BACN. The crystals thus obtained are in the form of finely divided powder which can eliminate the necessity of crushing after drying.

The temperature at which the Con-BACN solution is added to the alcohols mentioned above has no specific limitation so far as it is below the melting point of Con-BACN and normally ordinary temperatures may be applied.

The precipitated powder Con-BACN can be separated by a conventional method. For example, centrifugal separation, suction-filtration, spray drying may be used for the purpose.

According to a modification of the process for separating and recovering powder Con-BACN, the Con-BACN solution is added to a saturated aliphatic hydrocarbon having 5 to 9 carbon atoms instead of the monohydric alcohol of saturated aliphatic compounds having 3 to 5 carbon atoms. This modified process will be described in detail hereinbelow.

The type and amount of the organic solvent for the Con-BACN solution are same or similar to the case where the monohydric alcohol specified above is used.

According to the modified process, a reprecipitation process is employed, where the Con-BACN solution is added to a poor solvent to precipitate Con-BACN.

The poor solvent used in the modified process means saturated aliphatic hydrocarbons having 5 to 9 carbon atoms, whether normal-chained, branched or cyclic, and includes, for example: pentane, hexane, cyclohexane, methylcyclopentane, 2-methylpentane, 3-methylpentane, 2,2-dimethylbutane, 2,3-dimethylbutane, heptane, methylcyclohexane, 2-methylhexane, 3-methylhexane, 2,3-dimethylpentane, 2,4-dimethylpentane, octane, 2,2,3-trimethylpentane, 2,2,4-trimethylpentane, ethylcyclohexane, nonane and the like. From the views of commercial availability and economy hydrocarbons having 5 to 8 carbon atoms, such as pentane, hexane, cyclohexane, heptane, octane and 2,2,4-trimethylpentane are practically preferable. The above hydrocarbons may be used in single or in combination of two or more.

Saturated aliphatic hydrocarbons having 4 or less carbon atoms have a low boiling point so that the reprecipitation of Con-BACN under normal pressure at ordinary temperatures is hardly performed, and on the other hand, hydrocarbons having 10 or more carbon atoms have a boiling pont as high as 170° C. or higher so that subsequent handling, particularly drying of the resultant powder Con-BACN is difficult.

Further advantages of the saturated aliphatic hydrocarbons having 5 to 9 carbon atoms used in the present invention are that they can be easily separated by distillation due to their boiling points different from those of halogenated hydrocarbons or aromatic hydrocarbons and forming non-azeotropic mixture and thus can be reused.

The amount of these saturated aliphatic hydrocarbons to be used is normally from 1 to 20 times, preferably 2 to 10 times by volume of the amount of the Con-BACN solution. When the amount of the saturated hydrocarbon is less than the amount of the Con-BACN solution, the recovery ratio of Con-BACN is lowered, and on the other hand, the amount of the hydrocarbon exceeds 20 times of the Con-BACN solution, economical disadvantages are caused although there is caused no technical problem for the reprecipiration.

The reprecipitation of Con-BACN is performed by adding the Con-BACN solution to the aliphatic hydrocarbon, preferably with stirring. When the Con-BACN solution is added to the poor solvents, powder Con-BACN is precipitated in a very short time by virtue of excellent intercompatibility and interdispersibility between the good and poor solvents so that the good solvent remaining in Con-BACN can be efficiently extracted, and the resultant crystals are in the form of finely divided powder, which eliminates the necessity of crushing after drying.

Regarding the temperature at which the Con-BACN is added to the solvents there is no special limitation so far as it is below the melting point of Con-BACN, and normally ordinary temperatures may be employed.

The powder Con-BACN thus precipitated can be separated by a conventional method, such as centrifugal separation, suction filtration, and spray drying.

Further, according to the present invention, the Con-BACN slurry obtained by adding the Con-BACN solution to the poor solvent of saturated aliphatic hydrocarbons having 5 to 9 carbon atoms in the preceding step (hereinafter called Step (A)) is further distilled to removed the good solvent (hereinafter called Step (B)) and the Con-BACN slurry distilled in Step (B) is filtered to separate and recover Con-BACN in the powder form (hereinafter called Step (C)) and the filtrate is circulated (hereinafter called Step (D)) as the poor solvent used in Step (A).

In this case, in order to separate the good solvent by distillation in the distillation Step (B), it is desired that the poor solvents have a boiling point normally 5 degrees or more, preferably 10 degrees or more higher than that of the good solvents. Therefore, the good solvents and the poor solvents having different boiling points as above can be suitably combined. Typical combinations are such as; benzene (b.p. 80.1° C.)—heptane (93.6° C.), carbontetrachloride (76.8° C.)—2,2,4-trimethylpentane (99.2° C.) and ethylenedichloride (83.5° C.)—octane (125.7° C.). The most preferable combination is carbontetrachloride—2,2,4-trimethylpentane from aspect of the production process.

The Con-BACN slurry obtained in Step (A) is distilled to remove the good solvent.

The distillation can be performed under a normal or reduced pressure, and the distillation temperature is selected so as to maintain Con-BACN in the state of slurry without melting or solidifying. More specifically it is necessary that the distillation vessel is maintained at a temperature below the melting point of Con-BACN, say not higher than 120° C., preferably not higher than 100° C. According to the results of the experiments conducted by the present invention, if the Con-BACN slurry obtained in Step (A) is once filtered and the filtrate is distilled to recover the good solvent, Con-BACN dissolved in the filtrate will precipitate in a resin-like state and adheres onto the inside wall of the vessel or onto the stirring blades and solidifies thereon so that great difficulty is caused in stirring or handling, and hence difficulty in recovery of the solvent.

According to the present invention, the Con-BACN slurry is directly distilled so that Con-BACN dissolved in the solvent satisfactrily precipitate on the surfaces of powder in the slurry during the distillation, and no resin-like solidification of Con-BACN is caused. Therefore, it is possible to obtain a slurry of good powder Con-BACN, and to easily recover the good solvent. Regarding the removal of the good solvent from the Con-BACN slurry by distillation, a higher degree of removal is more preferably, and specifically 50% or higher removal is preferable. If the removal is lower than 50%, the recovery of Con-BACN is also lowered, and as the filtrate after distillation is circulated to be used in Step (A), part of the filtrate is required to be drawn out so as to maintain a constant proportion of the good solvent to the poor solvent as well as a constant concentration of Con-BACN in Step (A), and the amount of the filtrate to be drawn out is considerably large. Meanwhile, the good solvent recovered by distillation can be refined by fine distillation and can be re-used in the bromination of acenaphthane, condensation or dehydrobromination.

Then the Con-BACN slurry obtained in Step (B) is filtrated to separate and recover Con-BACN, and the filtrate is circulated to the poor solvent in Step (A). The filtration of the slurry may be done by a conventional method, such as suction filtration and centrifugal separation. In this way, Con-BACN is obtained in the form of finely divided powder after drying.

The filtrate is then circulated to the poor solvent in Step (A) to be used for the reprecipitation of Con-BACN. Specifically, part of the poor solvent is added to the filtrate containing Con-BACN, and the mixture is adjusted to a predetermined proportion of the good solvent and the poor solvent and is used as the poor solvent.

In this way, Con-BACN in the form of finely divided powder can be obtained with a high degree of yield from the Con-BACN solution prepared in Step (A), and as the filtrate is circulated for reuse, additional treatments of Con-BACN dissolved in the filtrate are not required as in the case of a batch-type reprecipitation process. Therefore, Con-BACN can be recovered with great industrial advantages.

DESCRIPTION OF PREFERRED EMBODIMENTS

Figure 1A:
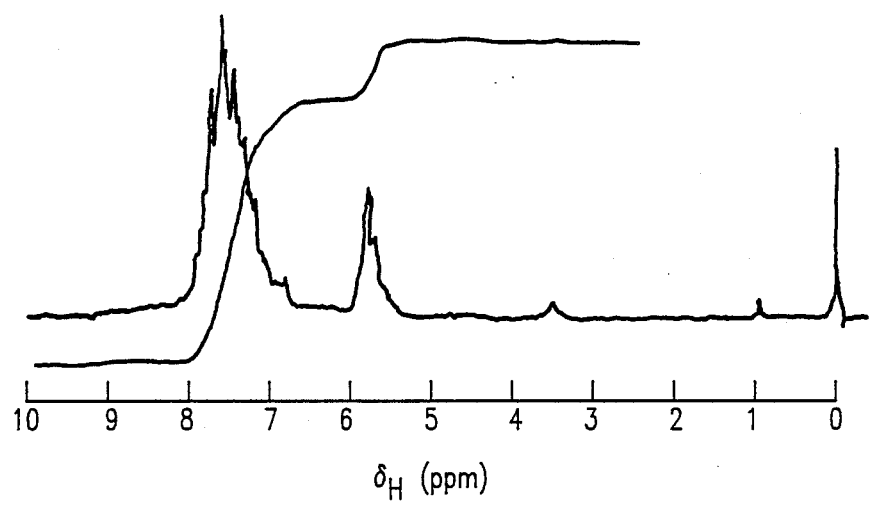
FIGS. 1 (a) and (b) are respectively a graph showing $^1$H—NMR spectrography for the intermediate, brominated acenaphthene condensate (a), and for the final product, Con-BACN.

In the following, more detailed explanations will be given with referring to Examples. However, this invention is not restricted by these Examples.

EXAMPLE 1

A mixture of 61.7 g of acenaphthene and 1.3 g of 2,2'-azo-bis(isobutyr)nitrile was added to 190 ml of carbon tetrachloride and the solution was heated for reflux at 77° C. To this solution was added 64.0 g of bromine dissolved in 90 ml of carbon tetrachloride dropwise while the solution was agitated for a whole hour. The reaction was continued for an additional half hour. After the reaction, the solution was cooled, 7.8 g of titanium tetrachloride was added at 25° C. to the solution, and the reaction continued for 2 hours at the same temperature. Subsequently 224 g of bromine was dropwise added for 3 hours to the solution at 25° C., the temperature was raised to 75° C. for reflux for additional 5 hours.

Then the reaction solution was cooled. The remaining bromine was removed by adding an aqueous solution of sodium hydrogen sulfite and the reaction solution was washed with 200 ml of a 1N solution of hydrochloric acid, followed by washing twice with each 300 ml of water. The reaction solution was then evaporated to dryness and the residue was dissolved in 250 ml of benzene. To this solution was added in drops 130 ml of a methanolic solution containing 25 g of potassium hydroxide. The mixture was refluxed for 2 hours under heating, then cooled. Salt of potassium bromide deposited was removed by filtration. Methanol was distilled and the remaining solution was washed three times with water. The concentrated benzene solution was dropwise added to acetone and 136.1 g of brominated acenaphthylene condensates was obtained as precipitant. Formula of the condensate obtained by the elemental analysis was $(C_{12}H_{5.0}Br_{2.9})_m$ and the yield from acenaphthene corresponded to 91.2%.

Followings are the melting point, elemental analysis and the degree of condensation obtained.

Melting point: 113° to 145° C.
Elemental analysis: C, 39.0; H, 1.4; Br, 60.2%.

| Degree of condensation by high performance liquid chromatography (GPC) | Monomer | 19% |
| --- | --- | --- |
| | Dimer | 27% |
| | Trimer to octomer | 54% |

The instrument for the high performance liquid chromatography and the condition of measurement are as follows:

Instrument: High speed liquid chromatograph (TSK HLC 802, Toyo Soda Mfg. Co., Ltd.).

Column: 7.5 mm inner diameter × 600 mm length.

Packing material: TSK GEL G1000H8 (Toyo Soda Mfg. Co., Ltd.)

EXAMPLE 2

In a reaction vessel equipped with an inner irradiation type high pressure mercury lamp were placed 61.7 g of acenaphthene and 190 ml of carbon tetrachloride, and the content was heated at 60° C. To this solution, a solution of 48.0 g of bromine in 70 ml of carbon tetrachloride was added in drops under stirring for an hour under irradiation of ultraviolet ray and the reaction continued for an additional half hour.

After the reaction, the solution was cooled to 25° C., 11.7 g of titanium tetrachloride was added to the reaction solution and the whole solution was kept for 2 hours under stirring.

Subsequently 240 g of bromine was dropwise added to the reaction solution at 25° C. for 3.5 hours, and then the mixture was refluxed under heating for 4 hours. Then the reaction solution was treated in the same manner as in Example 1 followed by the dehydrobromination reaction, to obtain 134.8 g of brominated acenaphthylene condensates.

Chemical formula obtained by the elemental analysis was $(C_{12}H_{4.8}Br_{2.9})_m$ and the yield from acenaphthene corresponded to 88.5%.

Melting point, elemental analysis and degree of condensation were estimated as follows:

Melting point: 108° to 123° C.
Elemental analysis: C, 37.8; H, 1.3; Br, 60.9%.

| Degree of condensation | Monomer | 22% |
| --- | --- | --- |
| | Dimer | 35% |
| | Trimer to octomer | 43% |

EXAMPLE 3

A mixture of 77 g of acenaphthene and 4.1 g of 2,2'-azo-bis(isobutyro)nitrile was added to 240 ml of carbon tetrachloride and refluxed under heating at 77° C. To this solution, a solution containing 80 g of bromine in 120 ml of carbon tetrachloride was added in drops under stirring in an hour and the reaction was continued for an additional hour. After the reaction, the solution was cooled to 30° C. and 8.1 g of iron (III) chloride was added, and the reaction was continued at the same temperature for additional 2 hours under stirring. To the reaction solution kept at 25° C., 240 g of bromine was dropwise added through a period of 3.5 hours, and then refluxed under heating for 2 hours until the color of bromine disappeared. The same treatment as in Example 1 and the dehydrobromination reaction were applied to the above solution, to obtain 143.8 g of brominated acenaphthylene condensates.

Chemical formula obtained by elemental analysis was $(C_{12}H_{5.0}Br_{2.3})_m$ and the yield from the acenaphthene corresponded to 86.4%.

Melting point, elemental analysis and degree of condensation of the condensates obtained were as follows:

Melting point: 132° to 160° C.
Elemental analysis: C, 43.4; H, 1.5; Br, 55.3%.

| Degree of condensation | Monomer | 21% |
| --- | --- | --- |
| | Dimer | 39% |
| | Trimer to octomer | 40% |

EXAMPLE 4

A mixture of 61.7 g of acenaphthene and 1.3 g of 2,2'-azo-bis(isobutyro)nitrile was added to 200 ml of carbon tetrachloride and the whole mixture was refluxed under heating at 77° C. To this solution was added in drops a solution of 96.0 g of bromine in 140 ml of carbon tetrachloride under stirring through a period of 1.3 hour, and the reaction was continued for an additional half hour. After the reaction, the solution was cooled and 6.5 g of iron (III) chloride was added to it, followed by reaction at 19° C. for an additional 2 hours. Subsequently 192 g of bromine was dropwise added through 3 hours to the reaction solution at 23° C., then the temperature was elevated to 78° C. and refluxed under heating for 3.5 hours. The same treatment as in Example 1 and the dehydrobromination reaction were applied to the above reaction solution, to obtain 135.8 g of brominated acenaphthylene condensates.

Chemical formula estimated from elemental analysis was $(C_{12}H_{5.0}Br_{2.7})_m$ and the yield from acenaphthene corresponded to 93.0%.

Melting point, elemental analysis and degree of condensation of the condensates obtained were as follows:
Melting point: 131° to 152° C.
Elemental analysis: C, 40.0; H, 1.4; Br, 59.9%.

| Degree of condensation | Monomer | 12% |
| --- | --- | --- |
| | Dimer | 25% |
| | Trimer to octomer | 63% |

EXAMPLE 5

A mixture of 61.7 g of acenaphthene and 1.9 g of benzoyl peroxide was added to 200 ml of carbon tetrachloride and the whole solution was refluxed under heating at 77° C. To this solution, a solution of 64 g of bromine in 90 ml of carbon tetrachloride was dropwise added under stirring through a period of 1.2 hours, and the reaction was continued for an additional half hour. After the reaction, the solution was cooled, mixed with 12.0 g of antimony pentachloride and reacted for 2 hours at 25° C. Subsequently 257 g of bromine was dropwise added to the reaction solution at 25° C. through a period of 3.4 hours. Then the temperature was elevated to 78° C. and the solution was refluxed under heating for 7 hours. This solution was treated in the same manner as in Example 1 and the dehydrobromination reaction followed, to obtain 170.1 g of brominated acenaphthylene condensates.

Chemical formula estimated from the elemental analysis was $(C_{12}H_{3.6}Br_{3.9})_m$ and the yield from acenaphthene corresponded to 92.5%.

Melting point, elemental analysis and degree of condensation of the condensates obtained were as follows:
Melting point: 162° to 175° C.
Elemental analysis: C, 31.4; H, 0.8; Br, 70.0%.

| Degree of condensation | Monomer | 16% |
| --- | --- | --- |
| | Dimer | 41% |
| | Trimer to octomer | 43% |

REFERENCE EXAMPLE 1

A mixture of 77 g of acenaphthene and 8.1 g of iron (III) chloride was added to 700 ml of carbon tetrachloride and the whole was kept at 20° C. To this solution, a solution of 480 g of bromine in 120 ml of carbon tetrachloride was added in drops through 4 hours under stirring. When the dropwise addition was completed, the temperature was elevated to 55° C. and the reaction was continued until the color of bromine disappeared. A dark brown insoluble matter formed in the reaction solution which amounted to 80 g was removed by filtration and the remaining solution was washed with hydrochloric acid and water, treated to apply the dehydrobromination reaction as in Example 1, to obtain 140 g of brominated acenaphthylene condensates.

Chemical formula estimated from the elemental analysis was $(C_{12}H_{3.4}Br_{4.2})_m$ and the yield from acenaphthene corresponded to 57.9%. The insoluble matter deposited in the process proved to monomers of brominated acenaphthene containing 75% of bromine.

Melting point, elemental analysis and degree of the brominated acenaphthylene condensates were as follows:
Melting point: 130° to 142° C.
Elemental analysis: C, 29.8; H, 0.7; Br, 69.3%.

| Degree of condensation | Monomer | 37% |
| --- | --- | --- |
| | Dimer | 43% |
| | Trimer to octomer | 20% |

EXAMPLE 6

A mixture of 308 g of acenaphthene and 6.6 g of 2,2'-azo-bis(isobutyro)nitrile was added to 950 ml of carbon tetrachloride and the whole mixture was refluxed under heating at 77° C. To this solution was dropwise added a solution of 320 g of bromine in 470 ml of carbon tetrachloride through 1.5 hours under stirring, and the reaction was continued for an additional half hour. After the reaction the solution was cooled, 38 g of titanium tetrachloride was added to the reaction solution at 25° C. and the solution was kept for an hour for the reaction. Then, 1120 g of bromine was added in drops through 4 hours at 25° C., then the temperature was elevated to 75° C. and the solution was refluxed under heating for 3 hours. After the completion of reaction, an aqueous solution of sodium hydrogen sulfite was added to remove unreacted bromine. The solution was washed with water and obtained 1500 ml of a carbon tetrachloride solution which contained 840 g of brominated acenaphthene condensates (corresponding to 2.0 moles of acenaphthene monomer as starting material). The brominated acenaphthene condensates were the compounds which contained 64.3% of bromine.

A 300 ml of fraction of this carbon tetrachloride solution which contained 168 g of brominated acenaphthene condensates was employed in the following dehydrobromination reaction.

In a stream of nitrogen, a solution consisting of 31.4 g of potassium hydroxide, 80 g of methanol and 32 g of water was added to the above solution and the reaction was continued under reflux at 58° C.

Figure 1B:
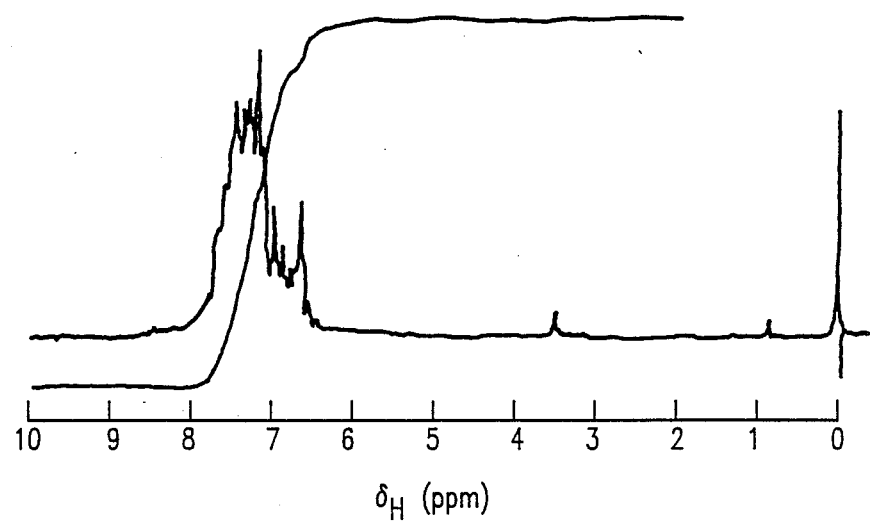

Time variation of the reaction was estimated by the $^1H$—NMR spectrum measurement, to obtain the rate of inversion from [I] to [II] of the general formulae. The $^1H$—NMR spectra before and after the reaction are shown in FIG. 1. In either spectrum, a peak corresponding to $^1H$ combined to the naphthalene ring is seen at $\delta_H = 7.0$ to 7.9 ppm. On the spectrum (a) for the intermediate compound a peak corresponding to the benzyl-position $^1H$ is observed at $\delta_H = 5.65$ to 5.9 ppm, while in the spectrum (b) for the final product this peak is shifted to $\delta_H = 6.7$ to 7.0 ppm and becomes less intense as a result of the double bond formation by the dehydrobromination reaction.

No peak corresponding to the by-product methylether was observed after the completion of reaction.

When the reaction was completed, the reaction solution was washed three times with water in an atmosphere of nitrogen. Then rate of decomposition of carbon tetrachloride was estimated by determining carbonate ion in the aqueous phase by the Orsat analysis.

Conditions of the reaction and results of analysis are tabulated in Table 1.

The obtained organic phase was added to 1.2 l of isooctane under stirring, to reprecipitate Con-BACN. Deposited powders were separated by filtration and dried, to obtain 110 g of Con-BACN which was reddish brown powders with bromine content 56.1% and the melting point 125° to 147° C. Analysis of the degree of condensation by the high speed liquid chromatography (GPC) gave 22% for monomer, 25% for dimer and 53% for the total of trimer to octomer. Further, 26% of Con-BACN was contained in the filtrate. Therefore, yield of Con-BACN through the reaction was almost quantitative.

EXAMPLE 7

To a 300 ml carbon tetrachloride solution containing 168 g of brominated acenaphthene condensates prepared in Example 6, a solution consisting of 31.4 g of potassium hydroxide, 105 g of methanol and 21 g of water was added in drops and the mixture was reacted at 58° C. under reflux. Results obtained are shown in Table 1.

EXAMPLE 8

To a 300 ml carbon tetrachloride solution containing 168 g of brominated acenaphthene condensates prepared in Example 6, a mixed solution of 56 g of a 40% sodium hydroxide solution (containing 22.4 g of sodium hydroxide) and 80 g of methanol was added in drops and the resulting mixture was refluxed at 58° C. Results obtained are shown in Table 1.

REFERENCE EXAMPLE 2

To a 300 ml carbon tetrachloride solution containing 168 g of brominated acenaphthene condensates prepared in Example 6, a solution of 31.4 g of solid sodium hydroxide in 120 g of methanol was dropwise added and the resulting mixture was refluxed to react at 58° C. An $^1$H—NMR analysis conducted after the reaction showed a peak at $\delta_H=4.0$ to 4.3 ppm which was assigned to a methylether bonding. Results obtained are shown in Table 1.

REFERENCE EXAMPLE 3

To a 300 ml carbon tetrachloride solution containing 168 g of the brominated acenaphthene condensates prepared in Example 6, a solution consisting of 31.4 g of sodium hydroxide, 75 g of methanol and 45 g of water was added in drops and the whole mixture was refluxed at 58° C. for reaction. Results obtained are shown in Table 1.

TABLE 1

| | | Example | | | Reference Example | |
|---|---|---|---|---|---|---|
| | | 6 | 7 | 8 | 2 | 3 |
| Condition of Reaction | Hydroxide of alkali metal | KOH | KOH | NaOH | KOH | KOH |
| | Ratio of water to alcohol (by weight) | 0.40 | 0.20 | 0.42 | 0 | 0.60 |

TABLE 1-continued

| | | Example | | | Reference Example | |
|---|---|---|---|---|---|---|
| | | 6 | 7 | 8 | 2 | 3 |
| | Time of reaction (hrs.) | 5 | 3 | 5 | 3 | 10 |
| Result | Rate of inversion (%) | 100 | 100 | 100 | 100 | 85 |
| | Degree of decomposition of carbon tetrachloride (%) | 0.5 | 0.6 | 0.5 | 2.0 | 0.4 |
| | By-production of methylether*[1] | x | x | x | O | x |

*[1] O and x mean "yes" and "no", respectively, for the by-production of methylether, as estimated by the $^1$H—NMR measurement.

EXAMPLE 9

A mixture of 411 g of acenaphthene and 8.8 g of 2,2'-azo-bis(isobutyro)nitrile was added to 1270 ml of carbon tetrachloride and the whole mixture was refluxed under heating at 77° C. To this solution, a solution of 427 g of bromine in 620 ml of carbon tetrachloride was dropwise added through 1.5 hours, and the reaction was continued for additional half an hour. After the completion of reaction, the reaction solution was cooled, 51 g of titanium tetrachloride was added to the solution at 25° C. and allowed to react for an hour. Subsequently 1490 g of bromine was added in drops through 4 hours at 25° C. Then the temperature was elevated to 75° C. and reflux was continued for 3 hours under heating. After the reaction, the reaction solution was mixed with an aqueous solution of sodium hydrogen sulfite to remove unreacted bromine, and the reaction solution was washed with water, to obtain a 2000 ml carbon tetrachloride solution containing 1120 g of brominated acenaphthene condensates (corresponding to 2.67 moles per monomer of raw material acenaphthene). The brominated acenaphthene condensates contained 64.3% of bromine.

Out of the carbon tetrachloride solution, a 112 ml solution which contained 62.9 g of brominated acenaphthene condensates (corresponding to 0.15 mole per acenaphthene monomer unit as raw material) was used for the following dehydrobromination reaction.

Figure 2:
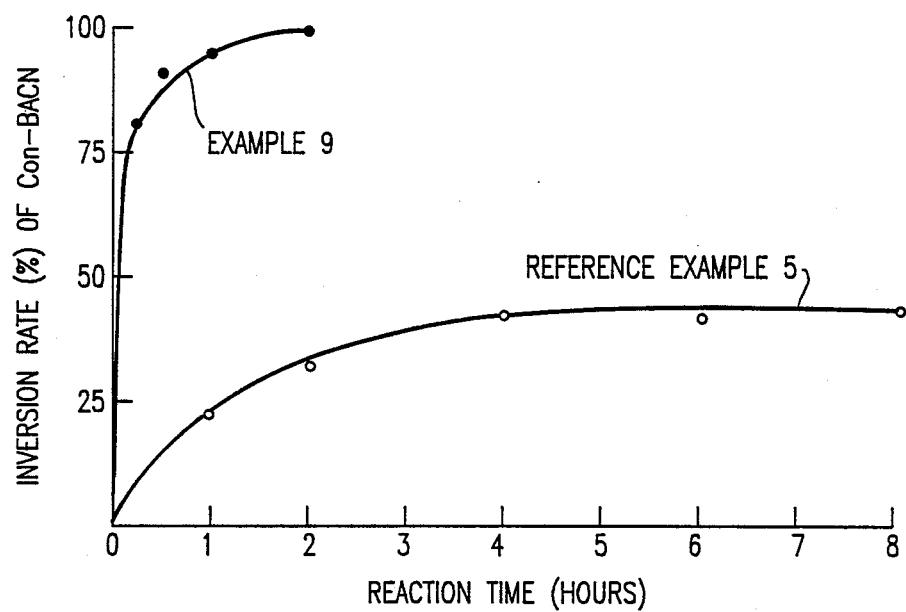
FIG. 2 is a graph showing the changes in inversion rates of brominated acenaphthene condensates in Example 9 and Reference Example 5.

To the above solution, 36.4 g of a 30% by weight aqueous solution of potassium hydroxide was added together with 0.48 g of tetra-n-butylammonium bromide in a stream of nitrogen and the whole mixture was refluxed at 74° C. under vigorous agitation. The reaction was traced for its time variation from the $^1$H—NMR spectrum measurements, to estimate the inversion rate from the general formula [I] to the general formula [II]. FIG. 1 shows a chart of $^1$H—NMR spectra for (a) brominated acenaphthene condensates and (b) Con-BACN as final product. FIG. 2 is a time variation of the inversion rate estimated from FIG. 1.

As is seen in FIG. 1, a peak corresponding to $^1$H combining to the naphthalene ring can be observed at $\delta_H=7.0$ to 7.9 ppm. With the intermediate (spectrum (a)), a peak corresponding to $^1$H at the benzyl position is seen at $\delta_H=5.65$ to 5.9 ppm, and a peak at $\delta_H=6.7$ to 7.0 ppm by the formation of a double bonding by the dehydrobromination reaction with Con-BACN (spectrum (b)) can be seen.

After the completion of the reaction, water was added to the reaction solution three times to wash the organic phase with water in an atmosphere of nitrogen.

The amount of carbonate ion in the aqueous phase was determined by the Orsat method, to obtain the decomposition rate of carbon tetrachloride.

The organic phase obtained was added to 450 ml of i-octane to reprecipitate Con-BACN. Powders deposited were separated by filtration and dried, to obtain reddish brown powders of Con-BACN in an amount of 41.2 g which showed a bromine content of 56.1% and a melting point of 125° to 147° C. The analysis of degree of condensation by high performance liquid chromatography resulted in 22% for monomer, 25% for dimer, and 53% for trimer to octomer. Further, the filtrate contained 9.7 g of Con-BACN. Therefore, the yield of Con-BACN after the completion of reaction was almost quantitative.

Figure 3:
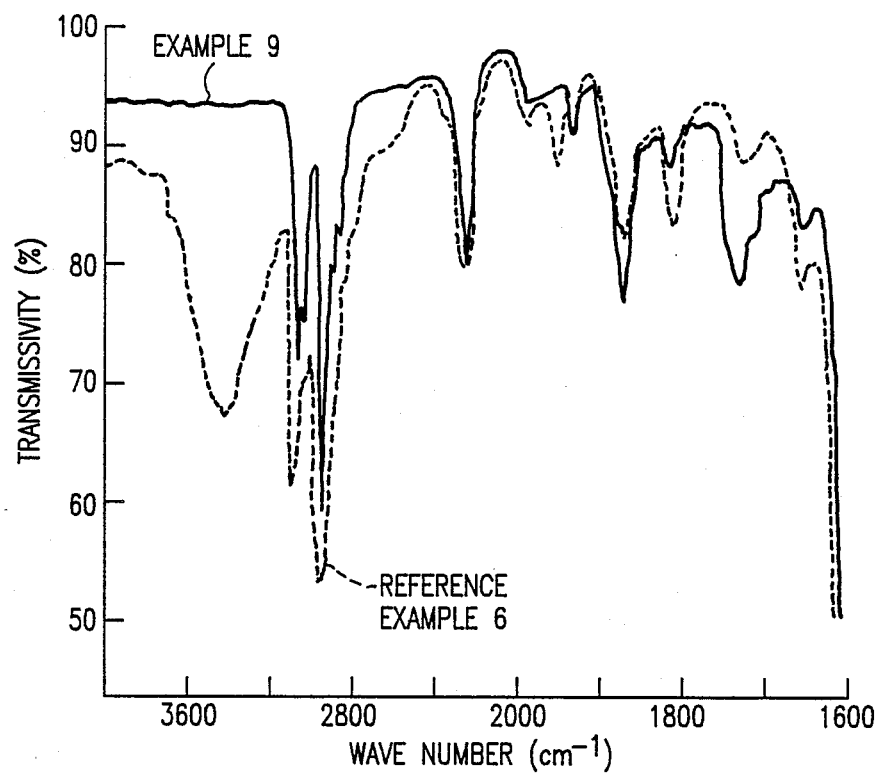
FIG. 3 is a graph showing infrared spectra of the final products in Example 9 and Reference Example 6.

In the next place, the obtained powdery sample was made a 5% (weight/volume) solution in carbon tetrachloride, and the infrared absorption analysis was made using a 1 mm thick quartz cell. Results were that, as shown in FIG. 3, no absorption peak at 3300 to 3700 $cm^{-1}$ assigned to OH groups could be seen, which demonstrates that there was contained no alcoholic compound of the brominated acenaphthene condensates. Table 2 shows the reaction condition and results of the analysis.

EXAMPLES 10-14

An aqueous solution of an inorganic metal base was added to a 112 ml solution of carbon tetrachloride containing 62.9 g of brominated acenaphthene condensates prepared in Example 9, and the whole mixture was brought into reaction with the same catalyst and temperature as in Table 2 under agitation. Analysis was conducted in a way similar to that in Example 9. Results obtained are shown in Table 2. In Example 14, however, the reaction was carried out using a 200 ml autoclave under a pressure at 100° C.

EXAMPLE 15

A 112 ml carbon tetrachloride solution containing 62.9 g of brominated acenaphthene condensates prepared in Example 9 was concentrated to dryness and the condensates obtained were dissolved in 120 ml of benzene. To this solution, 36 g of a 22% by weight aqueous solution of sodium hydroxide was added together with 0.48 g of tetra-n-butylammonium bromide and the whole mixture was vigorously stirred under reflux at 69° C. for 5 hours. After the reaction the organic phase was washed with water. The $^1$H-NMR measurement gave an inversion rate of 100% with respect to the brominated acenaphthene condensates. Then the organic phase was added to 450 ml of i-octane and Con-BACN was reprecipitated, to obtain 40.5 g Con-BACN in yellowish brown powders.

The powders showed almost the same values of bromine content, melting point and the composition of condensates as in Example 9. The infrared spectrum of the powders proved no by-product formation of alcohols.

REFERENCE EXAMPLE 4

To a 112 ml carbon tetrachloride solution of 62.9 g of brominated acenaphthene condensates prepared in Example 9, a solution of 10.9 g of solid sodium hydroxide in 40 g of methanol was dropwise added and the whole mixture was refluxed at 58° C. After the completion of reaction, the reaction solution was analyzed by $^1$H-NMR, in which a peak was observed at $\delta_H=4.0$ to 4.3 ppm corresponding to a methylether bonding. Results obtained are shown in Table 3.

REFERENCE EXAMPLE 5

To a 112 ml carbon tetrachloride solution of 62.9 g of brominated acenaphthene condensates prepared in Example 9, 27.3 g of a 40% by weight aqueous solution of potassium hydroxide was added and the whole mixture was refluxed under stirring at 74° C. After the completion of reaction, analysis was carried out as in Example 9. Results obtained are shown in Table 3 and the time variation of the reaction is shown in FIG. 2.

REFERENCE EXAMPLE 6

A 112 ml carbon tetrachloride solution of 62.9 g of brominated acenaphthene condensates prepared in Example 9 and 27.3 g of a 40% by weight aqueous solution of potassium hydroxide were placed in a 200 ml autoclave, and the reaction was conducted under pressure at 100° C. while the autoclave was vigorously shaked. After the completion of reaction, the reaction solution was washed with water, dried over anhydrous magnesium sulfate. Infrared spectrum measurement gave an absorption at 3300 to 3700 $cm^{-1}$ which is assigned to the OH group. This shows by-product formation of alcohols. Results obtained are shown in Table 3.

TABLE 2

| Condition of Reaction and Result | Example | | | | | |
|---|---|---|---|---|---|---|
| | 9 | 10 | 11 | 12 | 13 | 14 |
| Condition of Reaction | | | | | | |
| Inorganic metal base | KOH | NaOH | NaOH | NaOH | Na$_2$CO$_3$ | KOH |
| Quantity of the base (g) | 10.9 | 7.8 | 7.8 | 7.8 | 2.0 | 10.9 |
| Quantity of water (g) | 25.5 | 28 | 28 | 28 | 80 | 16.4 |
| Catalyst | Tetra-n-butylammonium bromide | Tetra-n-pentylammonium bromide | Tri-n-octylmethylammonium chloride | n-Octyltrimethylammonium bromide | Tetra-n-butylammonium bromide | Tetra-n-butylammonium bromide |
| Quantity of catalyst (g) | 0.48 | 0.57 | 0.61 | 0.38 | 1.44 | 0.48 |
| Reaction temperature (°C.) | 74 | 74 | 55 | 74 | 74 | 100 |
| Reaction time (hrs) | 2 | 4 | 4 | 3 | 7 | 1 |
| Result | | | | | | |
| Inversion rate (%) | 100 | 100 | 100 | 100 | 100 | 100 |
| Percentage of decomposed carbon tetrachloride | 0 | 0 | 0 | 0 | — | 0 |

TABLE 2-continued

| Condition of Reaction and | Example | | | | | |
|---|---|---|---|---|---|---|
| Result | 9 | 10 | 11 | 12 | 13 | 14 |
| By-product of alcohol*1 | x | x | x | x | x | x |
| By-product of methylether*2 | — | — | — | — | — | — |

For *1 and *2, see the Remarks on Table 3.

TABLE 3

| Condition of Reaction and Result | | Reference Example | | |
|---|---|---|---|---|
| | | 1 | 2 | 3 |
| Condition of Reaction | Inorganic metal base | KOH | KOH | KOH |
| | Quantity of the base (g) | 10.9 | 10.9 | 10.9 |
| | Quantity of water (g) | — | 16.4 | 16.4 |
| | Catalyst | — | — | — |
| | Quantity of catalyst (g) | — | — | — |
| | Reaction temperature (°C.) | 58 | 74 | 100 |
| | Reaction time (hrs) | 3 | 8 | 8 |
| Result | Inversion rate (%) | 100 | 44.4 | 62.0 |
| | Percentage of decomposed carbon tetrachloride (%) | 2.0 | 0 | 1.5 |
| | By-product of alcohol*1 | x | O | O |
| | By-product of methylether*2 | O | — | — |

*1By-production of alcohol was observed (O); not observed (x) on infrared absorption spectrum measurement.
*2O means that a by-product of methylether was observed on $^1$H—NMR measurement.

EXAMPLE 16

A mixture of 308 g of acenaphthene and 24 g of iron (III) chloride was added to 2.8 l of carbon tetrachloride and the whole mixture was maintained at 30° C. To this solution, a solution of 0.5 l of carbon tetrachloride was dropwise added through 5 hours, and heated to 55° C. to allow the reaction until the color of bromine disappeared. Then the solution was filtered to remove off non-dissolved matters and thoroughly washed with water. To this solution, a solution prepared by dissolving 114 g of potassium hydroxide in 0.6 l of methanol with heating and refluxing was added through one hour to allow the reaction for further one hour. The reaction solution was cooled, removed of potassium bromite by filtration and methanol by distillation, washed with water three times, and 3.6 l of carbon tetrachloride solution containing 620 g of Con-BACN was added thereto. The analysis of the resultant Con-BACN showed that it contained 67% bromine, and the condensation degree by the gel-permeation chromatograph measurements showed 35% for monomer, 42% for dimer and 23% for trimer to octomer.

0.45 l of this Con-BACN carbon tetrachloride containing 77.5 g of Con-BACN was subjected to the following reprecipitation.

The above Con-BACN carbon tetrachloride solution was dropwise added through 20 minutes at room temperature to 1.8 l of i-propanol under vigorous stirring by a laboratory disperser (manufactured by Mitamura Riken Kogyo K.K.). The dropwise addition instantaneously caused precipitation of fine powder particles, and after the completion of dropwise addition, the stirring was continued for further 20 minutes to completely precipitate the powder particles, which were separated by filtration and dried at 75° C. to obtain 70.5 g of brownish powder Con-BACN having a melting point from 125° to 145° C. The yield of Con-BACN from the Con-BACN carbon tatrachloride was equal to 91%.

EXAMPLE 17

0.45 l of the Con-BACN tetrachloride solution containing 77.5 g of Con-BACN prepared in Example 16 was dropwise added to 1.8 l of n-propanol under vigorous stirring by T. K. homomixer (manufactured by Tokushu Kika Kogyo K.K.) through 30 minutes at room temperature. The dropwise addition instantaneously caused precipitation of fine powder particles. The stirring was continued for further 20 minutes after completion of the dropwise addition, and the precipitate was filtered and dried to obtain 68.3 g of reddish brown powder Con-BACN having a melting point from 124° to 146° C. The yield of Con-BACN from the Con-BACN carbon tetrachloride solution was equal to 88.1%.

EXAMPLE 18

0.45 l of the Con-BACN tetrachloride solution prepared in Example 16 containing 77.5 g of Con-BACN was dropwise added to 1.8 l of tert-butanol under vigorous stirring at room temperature through 20 minutes. The dropwise addition instantaneously caused precipitation of fine powder particles. After completion of the dropwise addition, the stirring was continued for further 20 minutes, and the precipitate was filtered and dried to obtain 70.1 g of reddish brown powder Con-BACN having a melting point from 124° to 145° C. The yield of Con-BACN from the Con-BACN carbon tetrachloride solution was equal to 90.5%.

EXAMPLE 19

A mixture of 77 g of acenaphthene and 6 g of iron (III) chloride was added to 700 ml of carbon tetrachloride and the whole mixture was maintained at 30° C. To the solution thus obtained, a solution of 475 g of bromine and 125 ml of carbon tetrachloride was dropwise added through 4 hours. After completion of the dropwise addition, the solution was heated to 55° C. to allow the reaction until the color of bromine disappeared. The reaction solution was filtered to remove non-dissolved matter thoroughly washed with water, condensed and solidified. The residue was dissolved in 550 ml benzene. To the resultant solution, a solution prepared by dissolving 36 g of potassium hydroxide in 150 ml of methanol with heating and refluxing was dropwise added through one hour, and the reaction was caused for another one hour. The reaction solution thus obtained was cooled, then filtered to remove potassium bromide and distilled to remove methanol, and washed with water three times to obtain 600 ml of benzene solution containing 152 g of Con-BACN. The Con-BACN thus obtained contained 68% of bromine, and the gel-permeation chromatography measurements showed 36% for monomer, 43% for dimer and 21% for trimer to octomer.

The benzene solution was then dropwise added to 2.4 of n-amylalcohol under slow stirring by ordinary stirring blades at room temperature through 30 minutes. After completion of the dropwise addition, precipitation of powder particles was caused.

After completion of the dropwise addition, the stirring was continued for further 30 minutes, and the precipitate was filtered and dried. The resultant powder partially contained solid coagulated Con-BACN which could be finely divided easily by a home-size mixer to obtain 130.7 g of yellowish brown powder Con-BACN having a melting point from 126° to 146° C. The yield of Con-BACN from the benzene solution of Con-BACN was equal to 86%.

REFERENCE EXAMPLE 7

0.45 l of the carbon tetrachloride solution containing 77.5 g of Con-BACN prepared in Example 16 was dropwise added to 1.8 l of cold acetone (0°--10° C.) under stirring in a similar way as in Example 16. After the addition, the resultant powder particles were filtered out and dried to obtain 55.0 g of yellowish brown Con-BACN having a melting point from 126° to 146° C. The yield of Con-BACN from the carbon tetrachloride solution was equal to 71%.

EXAMPLE 20

A mixture of 231 g of acenaphthene and 18 g of iron (III) chloride was added to 2.1 l of carbon tetrachloride and the whole mixture was maintained at 25° C. To the solution thus obtained, 0.38 l of carbon tetrachloride was dropwise added through 5 hours, and then the solution was heated to 55° C. to proceed the reaction until the color of bromine disappeared. The solution was filtered to remove non-dissolved matters, which was washed thoroughly with water. To this solution, a solution prepared by dropping 108 g of potassium hydroxide of 0.45 l of methanol with heating and refluxing was dropwise added through one hour and the reaction was allowed for further one hour. The reaction solution was cooled, then filtered to remove potassium bromide distilled to remove methanol, and washed three times with water to obtain 2.7 l of a carbon tetrachloride solution containing 470 g of Con-BACN. The analysis of Con-BACN thus obtained showed a bromine content of 67% and the gel-permeation chromatography measurement of condensation degree showed 33% for monomer, 43% for dimer and 23% for trimer to octomer.

0.54 l of the above Con-BACN carbon tetrachloride solution containing 94 g of Con-BACN was subjected to reprecipitation. Thus the solution was dropped to 2.2 l of i-octane under stirring through 30 minutes. The addition instantaneously caused precipitation of fine powder particles. After completion of the dropwise addition, the stirring was continued for further ten minutes to completely precipitate powder particles. Then the precipitated Con-BACN was separated by filtration and the powder particles thus filtered were dried at 75° C. to obtain 78.0 g of reddish brown powder Con-BACN having a melting point from 126° to 147° C. The yield of Con-BACN from the Con-BACN carbon tetrachloride solution was equal to 83.0%. Then the filtrate was distilled to recover carbon tetrachloride and i-octane both with a purity of 98% or higher. When these recovered compounds were used in the subsequent reaction and reprecipitation, there was observed no problem.

EXAMPLE 21

0.54 l of the carbon tetrachloride solution prepared in Example 20 containing 94 g of Con-BACN was dropwise added to 2 l of n-hexane under stirring at room temperature through 30 minutes. The dropwise addition instantaneously caused precipitation of fine powder particles. After completion of the dropwise addition, the stirring was continued for further ten minutes and then the precipitated particles were filtered and dried to obtain 76.5 g of reddish brown Con-BACN having a melting point from 126° to 147° C. The yield of Con-BACN from the Con-BACN carbon tetrachloride solution was equal to 81.4%.

EXAMPLE 22

0.54 l of the carbon tetrachloride solution containing 94 g of Con-BACN prepared in Example 20 was dropwise added to 2.2 l of n-pentane under stirring at 15° C. to reprecipitate Con-BACN, and by a similar procedure as in Example 21, 71.9 g of reddish brown powder Con-BACN having a melting point from 125° to 147° C. was obtained. The yield of Con-BACN from the carbon tetrachloride solution was equal to 76.5%.

EXAMPLE 23

A mixture of 92.6 g of acenaphthene and 2.0 g of 2,2'-azo-bis(isobutyro)nitrile was added to 280 ml of carbon tetrachloride and heated to 77° C. and refluxed. To the solution thus obtained, a solution prepared by dissolving 96.0 g of bromine to 140 ml of carbon tetrachloride was dropwise added through one hour, and the reaction was continued for further half hour. After the reaction, the reaction solution was cooled. To this cooled solution 11.7 g of titanium tetrachloride was added at 25° C. to proceed the reaction for 3 hours at the temperature. Then 336 g of bromine was dropwise added to the reaction solution through four hours at 25° C., then the solution was heated to 75° C. to allow the reaction to proceed for five hours with heating and refluxing. Then after washing twice with water, the reaction solution was condensed and dried and then dissolved in 380 ml of benzene. To the solution thus obtained, a solution prepared by dissolving 38 g of potassium hydroxide in 200 ml of methanol was dropwise added to cause the reaction for two hours with heating and refluxing. The reaction solution was cooled to precipitate salts of potassium bromide and distilled to remove methanol which was washed three times with water to obtain 480 ml of benzene solution containing 222 g of Con-BACN.

The analysis of the resultant Con-BACN showed it contained 60.5% of bromine, and the measurements of condensation degree by gel-permeation chromatography showed 24% for monomer, 20% for dimer and 56% for trimer to octomer. Then the Con-BACN solution was dropwise added to 2 l of n-heptane under stirring at room temperature through one hour. The dropwise addition instantaneously caused precipitation of fine powder particles. After completion of the dropwise addition, the stirring was continued for further 30 minutes and the precipitated particles were filtered and dried at 75° C. to obtain 185.4 g of reddish brown powder Con-BACN having a melting point from 118° to 146° C.

The yield of Con-BACN from the benzene solution was equal to 83.5%. Then the filtrate was distilled to separate and recover benzene and n-heptane both with a purity of 98% or higher. There was observed no problem when these recovered compounds were used in the subsequent reactions and reprecipitation.

REFERENCE EXAMPLE 8

0.54 l of the carbon tetrachloride solution prepared in Example 20, containing 94 g of Con-BACN was dropwise added to 2.2 l of cold actone (0°--10° C.) under stirring. After completion of the dropwise addition, the precipitated powder particles were separated by filtration, and dried to obtain 65.8 g of yellowish brown powder Con-BACN having a melting point from 126° to 146° C. The yield of Con-BACN from the Con-BACN carbon tetrachloride solution was equal to 70%. The filtrate contained 28.2 g of Con-BACN as well as carbon tetrachloride and acetone, but the solvent formed a mixture of compounds having similar melting points so that it was impossible to separate carbon tetrachloride with a high purity by distillation.

EXAMPLE 24

A mixture of 154 g of acenaphthene and 12 g of iron (III) chloride was added to 1.5 l of carbon tetrachloride, and the whole mixture was maintained at 25° C. To the solution thus prepared, a solution prepared by dissolving 960 g of bromine in 250 ml of carbon tetrachloride was dropwise added through 5 hours. After completion of the dropwise addition, the solution was heated to 55° C. to cause the reaction until the color of bromine disappeared. Non-dissolved matters were removed by filtration and the reaction solution was thoroughly washed with water. Then a solution prepared by dissolving 72 g of potassium hydroxide in 300 ml of methanol with heating and refluxing was dropwise added thereto through one hour an the reaction was allowed for further one hour. After the reaction solution was cooled, the precipitated potassium bromide was removed by filtration and methanol was removed by distillation and washed with water to obtain 1.8 l of a solution contaning 310 g of Con-BACN and 1.7 of carbon tetrachloride. The solution thus obtained will be called "a treating solution" hereinafter.

This treating solution was subjected to the following steps of process.

Step (A)

The treating solution was dropwise added to 7.2 l of i-octane under stirring at room temperature through one hour to reprecipitate Con-BACN. The dropwise addition instantaneously caused precipitation of fine powder particles and the stirring was continued for further 30 minutes after completion of the dropwise addition to complete precipitation of powder particles.

Step (B)

The slurry of Con-BACN obtained in Step (A) was distilled with stirring under normal pressure in a distiller of 2.5 cm inner diameter and 80 cm height, filled with glass-made helix of 5 mm diameter, and distillation was completed with a vessel temperature from 85° to 95° C. and a tower top temperature from 76° to 83° C. to 2.3 l of distillation mainly composed of carbon tetrachloride. Then the slurry thus distilled was cooled to room temperature to obtain a slurry of Con-BACN having good dispersibility. The distillate was composed of 57.1 vol.% of carbon tetrachloride, and 42.9 vol.% of i-octane, which corresponded to 78% removal of carbon tetrachloride from the slurry charged in the distiller.

Step (C)

The Con-BACN slurry obtained in Step (B) was filtered under suction and the powder was separated from the filtrate. The powder thus obtainedwas dried to obtain reddish brown powder Con-BACN having a melting point from 125° to 147° C. The analysis of the powder Con-BACN showed a 67% bromine content, and measurements of the condensation degree by gel-permeation chromatography showed 33% for monomer, 43% for dimer and 23% for trimer to octomer. The filtrate contained 50 g of Con-BACN, 0.35 l of carbon tetrachloride and 5.8 l of i-octane, and mixed with 2.4 l of i-octane to be circulated to the poor solvent in Step (A).

Next, a freshly prepared treating solution was added to the poor solvent for reprecipitation in the same manner as in the first cycle of operation, and Steps (B) and (C) were performed in the same manner as in the first cycle. In this way, the whole process was repeated five times. The volume ratio of i-octane/CCl₄ at the time of reprecipitation in Step (A), the removal ratio of carbon tetrachloride in Step (B) and the yield ratio of Con-BACN are shown in Table 4.

The physical properties (melting point, composition of condensate and bromine content of the powder Con-BACN) obtained by the second or later cycles of process were almost the same as those of powder Con-BACN obtained by the first cycle of process.

All distillate obtained by the distillation through the first to fourth cycles of process was collected together and fine-distilled to obtain carbon tetrachloride of 99.5% purity, which could be successfully used for bromination, condensation and dehydrobromination in the fifth cycle of process without any technical problem.

REFERENCE EXAMPLE 9

0.55 l of carbon tetrachloride solution containing 94 g of Con-BACN, prepared in similar way as in Example 24 was dropwise added to 2 l of i-octane under stirring at room temperature through 30 minutes, and the stirring was continued for further 30 minutes to reprecipitate Con-BACN.

The powder precipitate was filtered and dried to obtain 76.6 g of reddish brown powder Con-BACN having a melting point from 126° to 147° C. The yield of Con-BACN from the tetrachloride solution was equal to 81.5%.

When the filtrate was distilled to recover carbon tetrachloride, severe scaling of viscous solid product was caused in the distiller vessel and the stirring was difficult to perform so that the recovering operaton could not be continued and carbon tetrachloride could not successfully be recovered.

TABLE 4

| Running Cycle No. | Volume ratio of i-octane/CCl₄ at the time of reprecipitation in Step (A) | Removal ratio of CCl₄ in Step (B) (%) | Yield ratio* of Con-BACN (%) |
| --- | --- | --- | --- |
| 1 | 4.2 | 78.0 | 84.0 |
| 2 | 4.0 | 83.2 | 98.2 |
| 3 | 3.9 | 78.5 | 97.5 |
| 4 | 4.0 | 82.0 | 98.0 |

TABLE 4-continued

| Running Cycle No. | Volume ratio of i-octane/CCl₄ at the time of reprepitation in Step (A) | Removal ratio of CCl₄ in Step (B) (%) | Yield ratio* of Con-BACN (%) |
|---|---|---|---|
| 5 | 4.1 | 83.6 | 98.5 |

*The yield ratio is percentage of the powder Con-BACN obtained by drying in each cycle of process to Con-BACN contained in the treating solution.

What we claim:

1. A process for producing brominated acenaphthylene condensates of the formula:

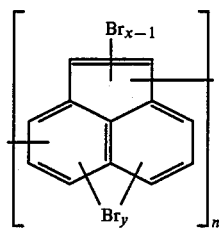

wherein x is 1 or 2, y is an integer from 1 to 6 and n is 2 or more, comprising:
   (A) brominating the side chain of the acenaphthene with 0.2 to 2.0 times as many moles of bromine as acenaphthene, said bromination initiated by ultraviolet radiation or by a radical initiator in a halogenated hydrocarbon solvent;
   (B) adding a Lewis acid catalyst to the reaction solution in step (A) to promote the condensation of the brominated acenaphthene product of step (A);
   (C) adding to the reaction solution of step (B) an equimolar or more amount of bromine relative to the amount of acenaphthene starting material, to further brominate and simultaneously condense the brominated acenaphthene and/or brominated acenaphthene condensates; and
   (D) dehydrobrominating the brominated acenaphthene condensates.

2. The process according to claim 1, in which the bromination in the step (A) is effected in the presence of a radical initiator.

3. The process according to claim 1, in which the dehydrobromination of step (D) is performed by adding an alkali metal hydroxide dissolved in a lower alcohol to a solution of brominated acenaphthene condensates dissolved in said halogenated hydrocarbon solvent.

4. The process according to claim 3, in which water is added to said alcohol so as to maintain the ratio of water to alcohol from 0.1 to 0.5 by weight.

5. The process according to claim 1, in which the dehydrobromination of step (D) is performed by bringing brominated acenaphthene condensate dissolved in an organic solvent which is immiscible with water into contact with an aqueous solution of an inorganic metal base in the presence of a phase transfer catalyst.

6. The process according to claim 5, wherein the phase transfer catalyst is a quaternary ammonium salt.

7. The process according to claim 5, wherein the inorganic metal base is selected from the group consisting of hydroxides, carbonates and hydrogen carbonates of alkali and alkaline earth metals.

8. The process according to claim 5, wherein the organic solvent immiscible with water is selected from the group consisting of halogenated hydrocarbons and aromatic hydrocarbons.

9. The process according to claim 1, which further comprises:
   (E) adding the solution of brominated acenaphthylene condensates obtained by said dehydrobromination step to a saturated $C_3$–$C_5$ monohydric alcohol to separate the said brominated acenaphthylene condensates in powder form.

10. The process according to claim 1, which further comprises:
    (F) adding the solution of brominated acenaphthylene condensates obtained by said dehydrobromination step to a saturated $C_5$–$C_9$ aliphatic hydrocarbon to separate said brominated acenaphthylene condensates in powder form.

11. The process according to claim 1, which further comprises:
    (G) adding a solution of brominated acenaphthylene condensates dissolved in an organic solvent to another organic solvent having a higher boiling point than the organic solvent to reprecipitate the brominated acenaphthylene condensates;
    (H) distilling the slurry of brominated acenaphthylene condensates obtained in step (G) to remove the organic solvent having a lower boiling point; and
    (I) filtering the slurry of brominated acenaphthylene condensates after the distillation of step (H) to separate the brominated acenaphthylene condensates in powder form and then circulating the filtrate obtained to step (G).

12. The process according to claim 11, in which the organic solvent having a lower boiling point is a halogenated hydrocarbon or aromatic hydrocarbon.

13. The process according to claim 11, in which the another organic solvent having a higher boiling point is a saturated aliphatic hydrocarbon having 5 to 9 carbons.

* * * * *